US012599735B2

(12) United States Patent
Sobel

(10) Patent No.: US 12,599,735 B2
(45) Date of Patent: Apr. 14, 2026

(54) ENDOTRACHEAL TUBE ATTACHMENT SYSTEM

(71) Applicant: Eitan Sobel, Rutland, VT (US)

(72) Inventor: Eitan Sobel, Rutland, VT (US)

( * ) Notice: Subject to any disclaimer, the term of this patent is extended or adjusted under 35 U.S.C. 154(b) by 1093 days.

(21) Appl. No.: 17/581,314

(22) Filed: Jan. 21, 2022

(65) Prior Publication Data

US 2023/0233783 A1 Jul. 27, 2023

(51) Int. Cl.
A61M 16/04 (2006.01)

(52) U.S. Cl.
CPC .............................. A61M 16/0418 (2014.02)

(58) Field of Classification Search
CPC ..................................................... A61M 16/04
See application file for complete search history.

(56) References Cited

U.S. PATENT DOCUMENTS

| | | | | |
|---|---|---|---|---|
| 4,848,331 A | * | 7/1989 | Northway-Meyer | ........................ A61M 16/0495 128/207.14 |
| 5,339,808 A | * | 8/1994 | Don Michael | .... A61M 16/0409 128/911 |
| 5,431,158 A | * | 7/1995 | Tirotta | .............. A61M 16/0488 128/207.14 |
| 6,543,446 B1 | * | 4/2003 | Christopher | ...... A61M 16/0488 128/207.14 |
| 6,763,831 B2 | * | 7/2004 | Sniadach | ............... A61B 13/00 128/207.14 |
| 6,792,943 B2 | * | 9/2004 | Kumar | .............. A61M 16/0488 128/200.26 |

* cited by examiner

*Primary Examiner* — Brandy S Lee
*Assistant Examiner* — Mishal Zahra Hussain

(57) ABSTRACT

An endotracheal tube interface apparatus including a enclosed space structure having integrated surrounding walls, a rearward wall and an internal volume, a first hollow stem disposed on the rearward facing wall and a second hollow stem disposed on the sidewall of the enclosed space structure, the first hollow stem accepting an endotracheal tube, the second hollow stem supporting an oxygen delivery tube, both first and second stems open to the internal volume of the enclosed space. The enclosed space structure may slide over the outside surface of the oral end of an endotracheal tube, inserted through the first hollow stem and wherein oxygen is delivered from a machine through an oxygen delivery tube attached over the second hollow stem, the oxygen entering the endotracheal tube after the internal volume of the enclosed space structure is pressurized.

5 Claims, 7 Drawing Sheets

100

*Section AA*

To Machine

ENDOTRACHEAL TUBE ATTACHMENT SYSTEM

CROSS-REFERENCE TO RELATED DOCUMENTS

The present invention claims priority to a U.S. provisional patent application No. 63/238,712, entitled MOVEMENT ENABLED ENDOTRACHEAL TUBE ATTACHMENTS, filed on Aug. 30, 2021, disclosure of which is included herein at least by reference.

BACKGROUND OF THE INVENTION

1. Field of the Invention

The present invention is in the field of medical devices and pertains particularly to methods and apparatus for securing an endotracheal tube to a patient.

2. Discussion of the State of the Art

In the art of patient intubation, an endotracheal tube apparatus is used commonly. An endotracheal tubing apparatus typically includes a transparent polyvinyl tube and inflatable cuff attached to the tracheal end, or the portion of the endotracheal tube inserted in a patient adjacent to the patients trachea. An endotracheal tube apparatus is adapted to be inserted into a patient's trachea, bypassing the vocal cords in order to keep the patient's airway open to receive oxygen and medical gasses during a period of time where the patient cannot otherwise breathe well because of a condition of an illness like pneumonia.

An endotracheal tube has a common length of about 33 centimeters in length and has a natural curvature that conforms to the curvature (Magill curve) of a patient's trachea (140 mm radius), with the patient's head held or confined in a neutral position. The cuff is positioned towards the tracheal end of the tube to seal off the trachea, so that material above the cuff) cannot enter the lung. The tracheal end of the tubing is also typically beveled to prevent tracheal damage during insertion.

There are general problems with the use of an endotracheal tube apparatus. For example, the oral end of the tube apparatus is typically secured to a patient's face with adhesive tape or a specialized clamping apparatus that does not permit longitudinal movement of the tube, to allow movement deeper into or out of the patient's trachea.

One limitation is that a patient's head should be kept relatively stable and in a neutral position while the endotracheal tube is inserted into the patient's throat and secured at the oral end of the tubing to reduce the prospect of longitudinal movement. If a patient moves their head upward, the tube may move deeper into the trachea. If the patient moves their head downward, the tube may back out of the trachea from the original depth inserted. Patients often make these movements inadvertently, without thinking. Such inadvertent movements may increase the risk of sub-glottic secretions, bypassing the cuff and entering the lungs, leading to ventilator associated pneumonia (VAP). Moreover, such movements may also lead to tracheal damage that may lead to risk of aspiration of the patient.

Therefore, what is clearly needed is an endotracheal attachment apparatus that corrects or eliminates the problems described above.

BRIEF SUMMARY OF THE INVENTION

According to an embodiment of the present invention, an endotracheal tube interface apparatus is provided, including a enclosed space structure having integrated surrounding walls, a rearward wall and an internal volume, a first hollow stem disposed on the rearward facing wall of the enclosed space structure, the first hollow stem having an inside diameter just larger than the outside diameter of an endotracheal tube apparatus, the inside diameter of the first hollow stem open into the internal volume of the enclosed space structure, a second hollow stem disposed on a surrounding wall of the enclosed space structure, the second hollow stem having an inside diameter roughly equal or larger than the inside diameter of the endotracheal tube and an external connection means to an oxygen delivery tube, the second hollow stem open into the internal volume of the enclosed space structure, wherein the oral end of an endotracheal tube inserted into the first hollow stem past the boundary into the internal volume of the enclosed space structure and can slide into and out of the enclosed space, and wherein oxygen is delivered from a machine through the oxygen delivery tube connected to the second hollow stem, the oxygen entering the endotracheal tube after the internal volume of the enclosed space structure is pressurized.

In one embodiment, the endotracheal tube interface apparatus further includes an elastic band having a width and a length; the elastic band attached at each open end to opposing sides of the enclosed space structure; the elastic band of sufficient length and elasticity to hold the enclosed space structure at a patient's front side, using the back side of the patient's head and neck to loosely secure the enclosed space. In one embodiment, the endotracheal tube interface apparatus further includes a neck collar having a pair of positional mounting arms attached to opposing sides of the enclosed space structure; the neck collar securing the enclosed space structure at the patient's front side, using the patient's neck and clavicles; the collar functioning to limit the upward and downward movement of the patient's head.

In one embodiment, the first hollow stem is elongated, conforming to the Magellan curve of the endotracheal tube apparatus and wherein the first hollow stem is inserted into the patient's mouth during use. In another embodiment, the first hollow stem is a short ring that is straight, which remains outside of the patient's mouth during use. In one embodiment, the endotracheal tube interface apparatus further includes a section of flex tubing attached at one end to a fitting installed on the oral end of the endotracheal tube and at the other end to the second hollow stem inside of the internal volume of the enclosed space structure.

In one embodiment, the enclosed space structure is closed except for the openings created by the first and second hollow stems. In another embodiment, there are other potential openings and possibly opening covers used for various purposes such as manipulating parts in the internal volume, cleaning the internal volume, evacuating gases, measuring pressures and so forth. In one embodiment, the enclosed space structure is molded with the first and second hollow stems to form one contiguous piece. Size and stem dimensions are adapted to fit the various tubing sizes of the endotracheal tube apparatuses, relative to the gender and age group of the patient. In an embodiment using a collar, the collar may be expanded to fit around a patient's neck and wherein the collar may be fastened at the rear, using common hardware.

In one embodiment, the endotracheal tube interface further includes at least one inflatable cuff mounted on a sliding thin tube with an internal diameter slightly larger than the external diameter of the endotracheal tube and the inflatable cuff and tube are mounted over the tracheal side of the endotracheal tube, capable of some longitudinal movements along the endotracheal tube between two stop points of the endotracheal tube, and wherein the endotracheal tube may slide a small distance through the inflatable cuff tube if pull force or push force is applied to the tube. In one embodiment, the endotracheal tube interface further includes a lubricant for lubricating the inside diameter of the first hollow stem to reduce friction between the inside diameter of the first hollow stem and the outside diameter of the endotracheal tube. In one embodiment, the second hollow stem is elongated and has a curvature toward the rear wall of the enclosed space structure. In one embodiment, the rearward facing wall is shaped ergonomically to conform generally to the shape of the patient's mouth and chin area.

DETAILED DESCRIPTION OF THE INVENTION

In various embodiments described in enabling detail herein, the inventor provides a unique system for enabling endotracheal attachment to a patient that allows for movement of the endotracheal tubing within a tube interfacing enclosed space. It is a goal of the present invention to enable an endotracheal tube to be longitudinally contained at the patient's oral end in a manner that provides for frictional movement between the tube and a tube housing feature of the enclosed space tube interface. Another object of the invention is to obfuscate a requirement for adhesive tape and other ad hoc means of attaching the endotracheal apparatus to a patient. The present invention is described using the following examples, which may describe more than one relevant embodiment falling within the scope of the invention.

Figure 1:
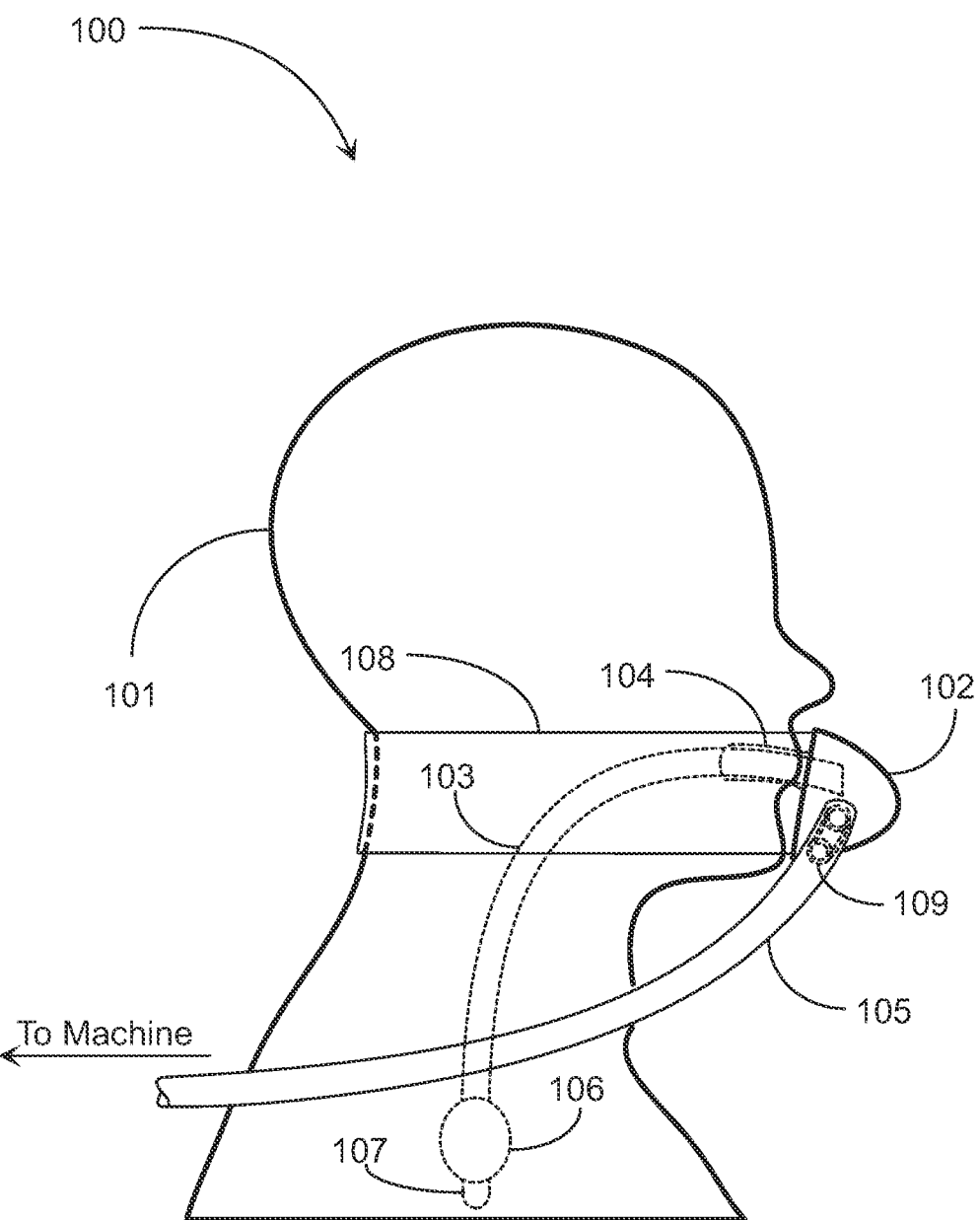
FIG. 1 is a side elevation view of an endotracheal tube attachment system according to an embodiment of the present invention.

FIG. 1 is a side elevation view of endotracheal tube attachment system 100, according to an embodiment of the present invention. Endotracheal tube attachment system (ETAS) 100 is adapted for a patient, 101, to be worn under intubation for a respiratory illness or under certain conditions of surgery or other treatments where the patient, 101, requires oxygen gasses delivered by a ventilator machine. ETAS 100 includes a plastic tube interfacing enclosed space, 102. Enclosed space 102 is adapted to function as a loosely-worn bridge between the oral disposed end of an endotracheal tube apparatus, 103 and a ventilator oxygen delivery tube, 105. ETAS 100 Enclosed space 102 includes integrated surrounding walls, a rearward wall resting on a user's face and/or lips. ETAS 100 is used to deliver medical gasses such as Oxygen, Nitrogen, CO2 and medications.

Enclosed space 102 may be molded from a medical grade plastic having a generally low coefficient for friction, such as polyetheretherketone (PEEK), ultra high molecular weight polyethylene (UHMWPE), or other thermoplastics like polydicyclopentadiene (PDCPD). Such materials have properties that are important to the successful practice of the present invention, including: low friction rating, high temperature tolerance, chemical corrosive resistance and general damage resistance. In a preferred embodiment, enclosed space 102 is opaque, so that the patient may not be able to see the secured tubing, thereby reducing the potential for anxiety in general. However, in some embodiments, enclosed space 102 may be translucent.

Enclosed space 102 is hollow, having surrounding walls and an rearward wall that may be ergonomically formed to conform to the general shapes of the patient 101 in the area of the lips and chin area beneath the patient's nose. In one embodiment, the material used to fabricate enclosed space 102 is moderately pliable such that conformity against the shape of the patient's face is more easily achieved. Enclosed space 102 includes hollow stem 104, having a slightly curved trajectory, projecting a distance from the back wall of enclosed space 102. Stem 104 is adapted to receive endotracheal tubing 103, through the inside diameter thereof, into the internal volume of enclosed space 102.

Stem 104 may be a contiguous part of the material used to fabricate enclosed space 102. Stem 104 has an inside diameter that is open into the interior of enclosed space 102. Stem 104 is adapted to be inserted into the mouth of patient 101 during intubation. The inside diameter of stem 104 is just larger than the outside diameter of an endotracheal tube 103, which may be a stock diameter endotracheal tube. Enclosed space 102 includes a second hollow stem 109, having a slightly curved trajectory, projecting a distance from the sidewall of enclosed space 102. Second stem 109 may be a contiguous part of the material of enclosed space 102.

Second stem 109 has a connector means to the oxygen delivery tube 109 and opens into the interior of enclosed space 102. In one embodiment, the outside diameter of second stem 109 is smaller than the inside diameter of oxygen delivery tube 105. The elasticity of tube 105 enables the tube to be stretched over second stem 109. In one embodiment, the fit is a tight fit that may be reinforced by a hose clamp or other restrictive clamp. In other embodiments, hose fittings may be provided to connect an oxygen delivery tube to second stem 109. The distal end of delivery tube 105 may be connected to a ventilator machine or a machine that delivers oxygen under pressure. Connection between the second stem 109 and delivery tube 105 may be done is various ways, including implementing a small piece of adjusting tube between tube 105 and the second stem 109. Additionally, a gasket or membrane could be implemented in a seal.

Inside diameters for tubes 103 and 105 are not depicted in this view but may be assumed present and of stock diameters for the age and gender of patients. For example, tube 103 for an adult male may have a nominal inside diameter of 9.0 mm while tube 103 for an adult female may have a nominal inside diameter of 8.0 mm. Tube 103 for a smaller child or infant will have a much smaller inside diameter. It may be noted herein that enclosed space 102 may be scaled in size with respect to the general size and requirements of patients. For example, the internal volume of a enclosed space for a small child may be much smaller than a enclosed space sized for an adult male.

In this embodiment, endotracheal tube 103 includes a beveled distal end 107 and an inflatable tube cuff, 106, positioned just above the distal end of tube 103. It is duly noted herein that there may be a small opening through tubing 103 (not illustrated), just above the beveled end, 107, adapted to enable gas to escape the tubing. Such an opening is generally termed a Murphy eye in the art. Also noted herein, cuff 106 may include a cuff inflation line (not illustrated), typically secured alongside tubing 103, with a proximal connection to a cuff inflation device or machine. The aforementioned accessories are not necessarily modified to practice with the present invention and therefore are removed from view in this embodiment for the purpose of clarity.

In this embodiment, oxygen delivery tube 105 is not directly connected to endotracheal tube 103 within enclosed space 102. Rather, oxygen is delivered into the volume inside enclosed space 102 and the enclosed space pressure forces the oxygen through stem 104, through endotracheal tube 103 and into the lungs of the patient, 101. Enclosed space 102 is worn by patient 101, in this case, using a flexible strap, 108, that loosely holds enclosed space 102 in place against the patient's mouth and upper chin area. In this embodiment, flexible strap 108 may be an elastic strap that may be stretched over the patient's head and secured behind the attachment system, 100, at the rear of the neck of patient 101. In another embodiment, enclosed space 102 may be secured against the mouth and chin area of patient 101 using a pair of elastic ear straps, without departing from the spirit and scope of the present invention.

In a preferred embodiment, endotracheal tube 103 may slide more into the internal volume of enclosed space 102 or more out of the internal volume of enclosed space 102, as enabled by a low friction slip fit between the outside of tube 103 and the inside of hollow stem 104. Patient 101 may therefore make inadvertent movements of the head upwards or downwards without pulling on or pushing inward on tube 103. Patient 101 may also pull out on enclosed space 102 without dislodging endotracheal tube 103 from its inserted position and depth.

In one embodiment, the enclosed space 102, more particularly stem 104, prevents the proximal unconnected end of endotracheal tube 103 from exiting enclosed space 102 via egress from step 104. In one embodiment, a lubricant may be used between the outside diameter of the endotracheal tube and the inside diameter of stem 104 of enclosed space 102, to reduce or eliminate any air leakage from enclosed space 102 into the patient's mouth. In a preferred embodiment enclosed space 102 is a fixed piece and does not move in relation to contained and connected elements. The contained and connected elements move, but the enclosed space remains static in relation to the user. In another embodiment, the enclosed space can be removed or replaced for various reasons.

Figure 2A:
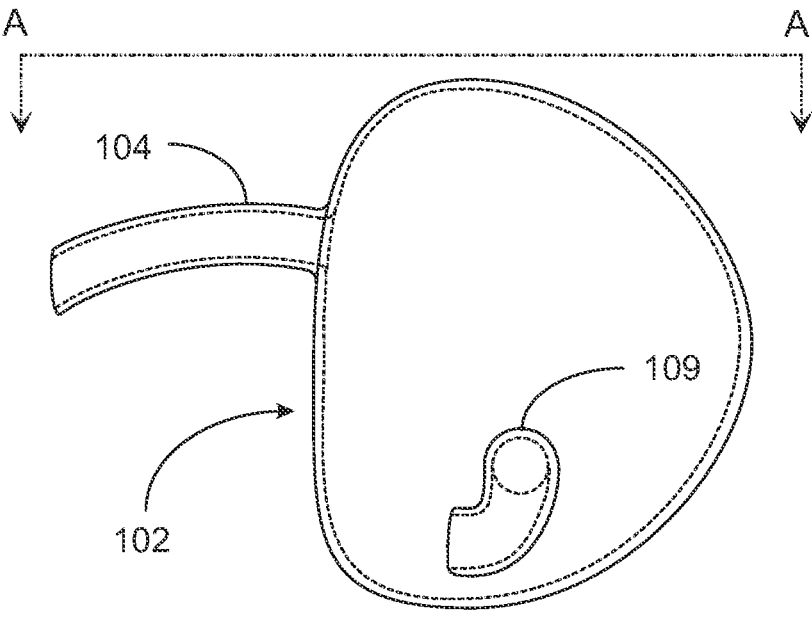
FIG. 2A is a side elevation of the tube interfacing enclosed space of FIG. 1.

FIG. 2A is a side elevation of tube interfacing enclosed space 102 of FIG. 1. Enclosed space 102 is fully closed in this embodiment, except for the opening through stem 104 and the opening, through second stem 109. Stem 104 may extend to the patient's mouth and may conform to the curvature of the endotracheal tubing known in the art as a "Magill Curve". Stem 104 is roughly centered on the back wall of enclosed space 102 and is located further up on the Y axis of the enclosed space.

Second stem 109 is generally located on the Y axis of the profile of the enclosed space, further down, below the horizontal X axis. Second stem 109 extends outward and then towards the rear of enclosed space 102, in a direction that would point generally behind the patient receiving treatment. The patient wearing enclosed space ETAS 100 faces generally away from equipment, such as a ventilator machine, in most embodiments. The direction of extension of second stem 109 is not critical to the practice of the invention. The direction of extension of second stem 109 may be in another general direction, without departing from the spirit and scope of the present invention. Likewise, the overall length of second stem 109 is not relevant to the practice of the invention. It should, however, be of sufficient length to secure the oxygen delivery hose over some surface distance, to the base thereof.

Figure 2B:
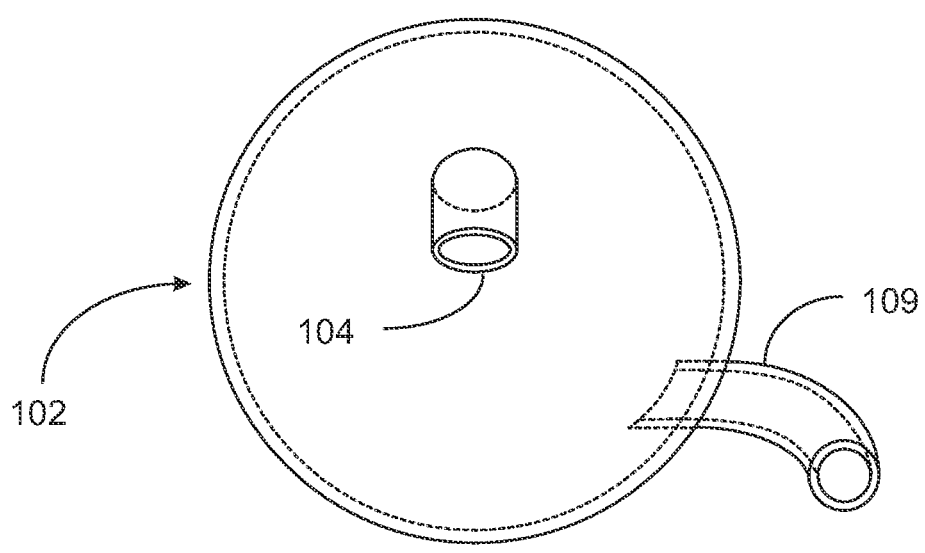
FIG. 2B is a rear elevation view of the tube interfacing enclosed space of FIG. 1.

FIG. 2B is a rear elevation view of tube interfacing enclosed space 102 of FIG. 1. In this view, stem 104 is roughly centered on the Y axis above the horizontal X axis and faces toward the patient. Stem 104 may extend almost completely into a patient's mouth during use, with the patient's lips touching the rear wall of enclosed space 102. Second stem 109, adapted to receive the oxygen delivery tube, may be located about half-way up the enclosed structure so the oxygen line does not interfere with the patient's face or clothing. Enclosed space 102 may be an annular, elliptical or any other shape of the enclosed space, without departing from the spirit and scope of the present invention. Enclosed space 102's size may be scaled in size as described further above. A large enclosed space for an adult male may have a much larger internal volume than a smaller enclosed space 102 for a small child. In general use, when oxygen is delivered through second stem 109 into the enclosed space interior, the interior volume is saturated and pressure inside the enclosed space is equalized, forcing the gas into the open end of the endotracheal tube and into the patient's lungs.

Figure 3A:
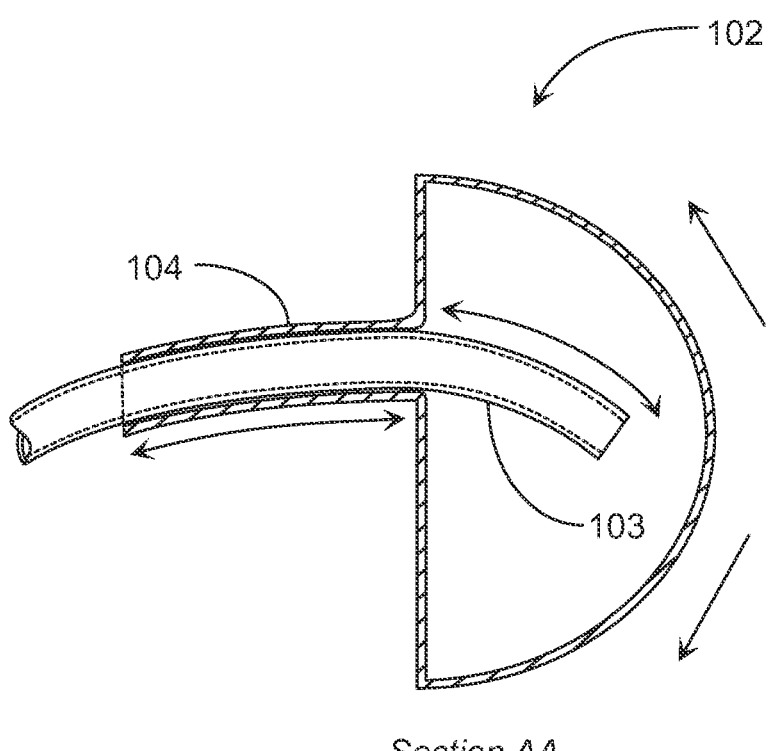
FIG. 3A is a sectioned view of the tube interfacing enclosed space of FIG. 2A taken along section line AA.

FIG. 3A is a sectioned view of tube interfacing enclosed space 102 of FIG. 2A, taken along section line AA. In this sectioned view, the second stem 109, depicted in FIG. 2A is removed. In this view, endotracheal tube 103 is depicted in part, inserted through stem 104 and into the interior of enclosed space 102. As a result of inadvertent movement of or force against enclosed space structure 102 generally, according to the directional arrows, tube 103 may remain stable, while stem 104 may slide in either direction over the tube, according to the double arrows. The open end of tube 103 may advance further into enclosed space 102 or may advance further out of enclosed space 102 through stem 104, depending upon the movement of enclosed space 102 over the outside surface of the endotracheal tube 103, represented generally by the directional arrows. When the patient looks upwards or downwards, or when the patient pulls out on enclosed space 102, the endotracheal tube with an inflated cuff stays in place, reducing or eliminating potential injury and discomfort.

Figure 3B:
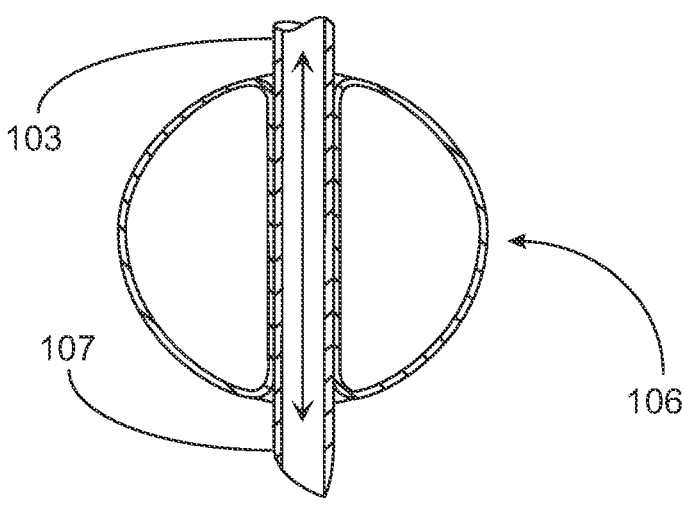
FIG. 3B is a sectioned view of the inflatable cuff on a sleeve of FIG. 1.

FIG. 3B is a sectioned view of inflatable cuff 106 of FIG. 1. Inflatable cuff 106 is adapted to be inflated after insertion to prevent any secretions from entering a patient's lungs. A cuff inflation line and valve, as well as a Murphy's eye opening, typically placed near the beveled end of the endotracheal tube 103, are not illustrated in this example but may be assumed present. In some embodiments, a cuff is not required in order to practice the present invention; in some cases, such as with pediatric patients, cuffs are not used. In one embodiment, a suction line may also be present and may be part of the endotracheal tubing apparatus. In one embodiment, at least one inflatable cuff 106 is mounted on a sliding thin tube with an internal diameter slightly larger than the external diameter of the endotracheal tube 107. The sliding thin tube slides along the endotracheal tube between two stop points. A stop point can be a ring or a ridge formed contiguously with the endotracheal tubing 107.

Figure 3D:
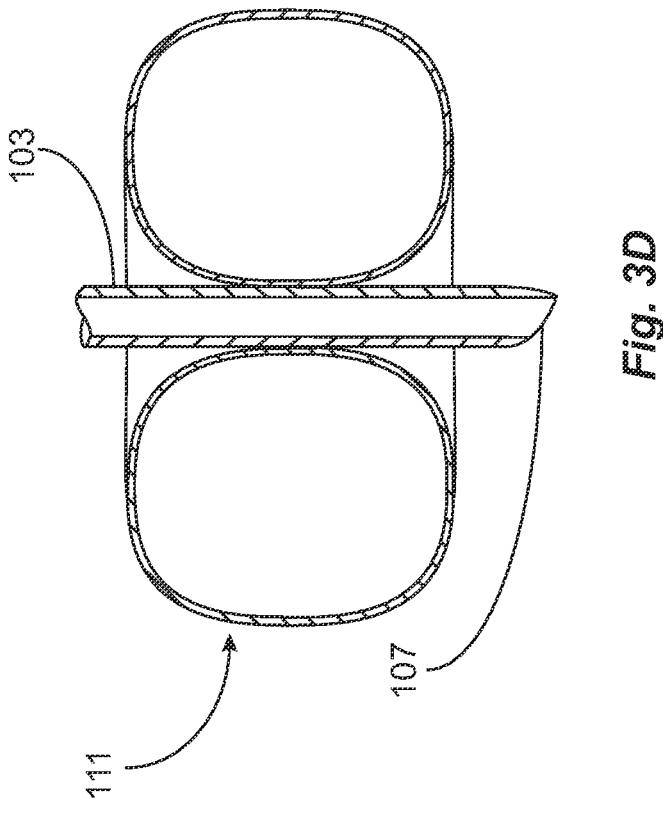
FIG. 3D is a sectioned view of a narrow base distortable inflatable cuff
Figure 3C:
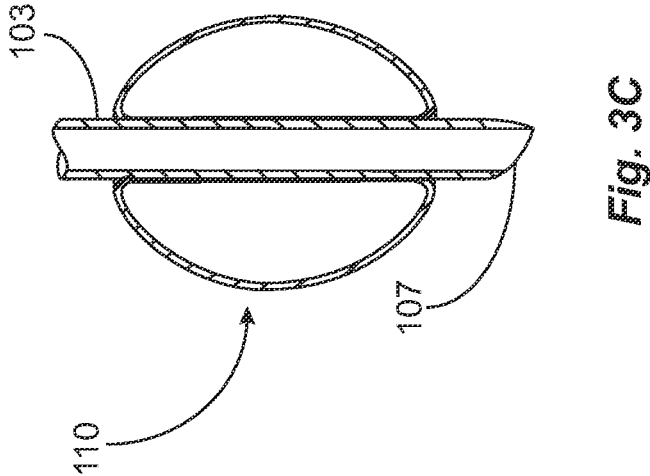
FIG. 3C is a sectioned view of a current wide base inflatable cuff of FIG. 1.
Figures 3E, 3F:
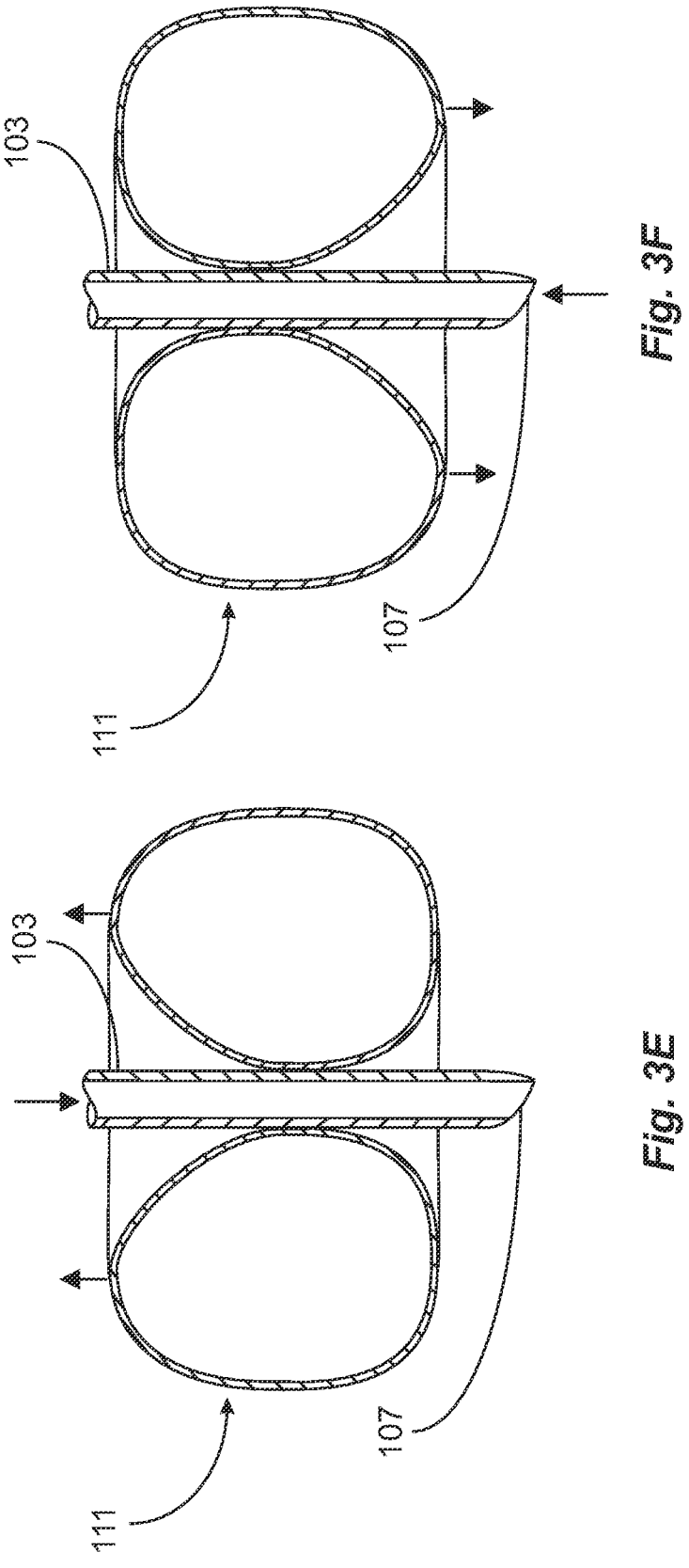
FIG. 3E is a narrow base distortable inflatable cuff of FIG. 3D that is pushed down.
FIG. 3F is a narrow base distortable inflatable cuff of FIG. 3D that is pulled up.

FIG. 3C is a cuff design having a wide base attached to the endotracheal tube wherein when inflated, the top of the cuff is pressing against the trachea mucosa of the tracheal wall (not shown). FIG. 3D is a distortion enabled cuff wherein the cuff has a narrow base attached to the endotracheal tube. FIG. 3E is the distortion enabled cuff of FIG. 3D, wherein the endotracheal tube is pushed downward, and the cuff is distorted upward, thereby allowing slight movement of the endotracheal tube downwards without scraping the tracheal mucosa. FIG. 3F is the distortion enabled cuff of FIG. 3D, wherein the endotracheal tube is pulled upward, the cuff is distorted downward, thereby allowing slight movement of the endotracheal tube upwards without scraping the tracheal mucosa. In another embodiment, one or distorted cuffs are used to seal the trachea and allow some movements of the endotracheal tube at the tracheal end.

Figure 4:
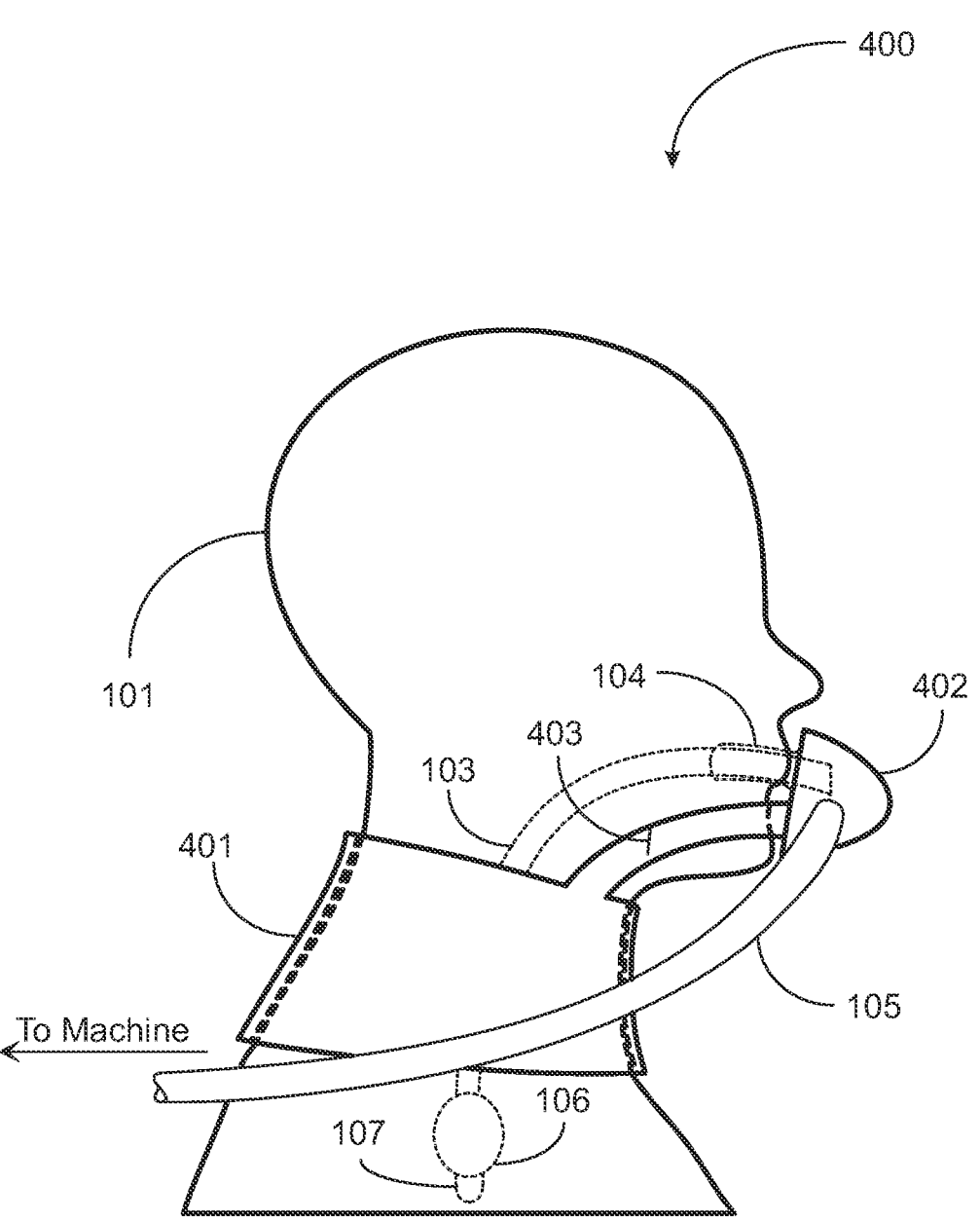
FIG. 4 is a side elevation view of an endotracheal tube attachment system according to another embodiment of the present invention.

FIG. 4 is a side elevation view of an endotracheal tube attachment system 400, according to another embodiment of the present invention. Endotracheal tube attachment system 400 is very similar to system 100 described in FIG. 1, with an exception that a neck collar, 401, is provided and used to limit movement of the head of patient 101; and that a enclosed space, 402, analogous in materials and function to enclosed space 102 is mounted to or otherwise a fixed part of collar 402. Enclosed space 402 is held in place relative to collar 401 by a pair of mounting arms, 403. Enclosed space 402 may be adapted to snap onto or otherwise be mounted to mounting arms 403, which in one embodiment may be adjustable somewhat in length to compensate for physical differences in patients.

Collar 401 may cover the front of a patient's neck area and may be fastened at the back of the patient's neck using hook and loop fasteners, snap buttons, a zipper interface, or other methods. Collar 401 may be fabricated of a relatively stiff but flexible material to enable opening the collar to fit the collar around a patient's neck. In one embodiment, enclosed space mounting arms 403 are a contiguous part of collar 401 and are made of the same material. In another embodiment, enclosed space 402 is securely mounted to the ends of each mounting arm 403 but may be a removable part that may be sterilized separately from the collar materials.

In this embodiment, the tube interface is the same as the tube interface in the embodiment of FIG. 1. Mounting arms 403 make enclosed space 402 less moveable, and collar 401 limits the amount of upward or downward movement of the patient's head. In one embodiment, both the enclosed space 402 interface and cuff 106 interface allow for longitudinal movement of the endotracheal tube 103. Collar 401 may be scaled up or down in size in proportion to the enclosed space and dimensions of the tubing material as required for differences in patient gender and age group. Collar 401 is not required in order to practice the present invention, but may provide assurance of less movement of the head of patient 101 and less movement of enclosed space 402 over the endotracheal tube, 103.

Figure 5:
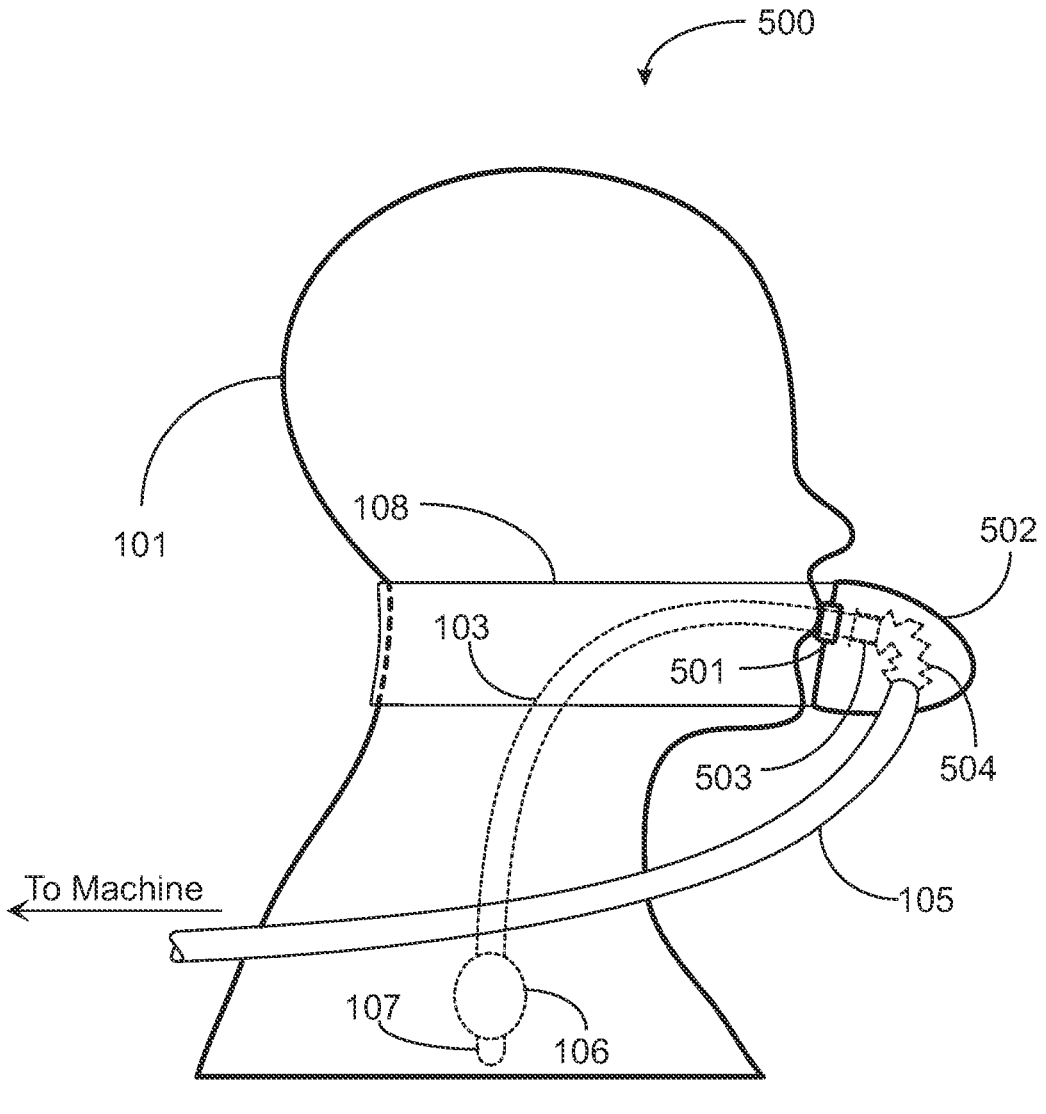
FIG. 5 is a side elevation view of an endotracheal tube attachment system according to a further embodiment of the present invention.

FIG. 5 is a side elevation view of an endotracheal tube attachment system 500, according to a further embodiment of the present invention. Endotracheal tube attachment system 500 is adapted to function much in the same way as the endotracheal tube attachment system of FIG. 1 or of FIG. 4. In this embodiment, an enclosed space, 502, is provided and includes a different design than enclosed space 102 or enclosed space 402 described above. In this embodiment, the oral end of endotracheal tube 103 includes a fitting, 503, that may be a plastic fitting that fits tightly over the very end of the tube. A pliable flex tubing, 504, is provided in this example that attached to the oral end of tube 103 and extends to and is attached to the second stem (not visible) that supports oxygen delivery tube 105. In this embodiment, a short ring, 501, is adapted to receive endotracheal tube 103 there through as previously described relative to stem 104 on enclosed space 102 of FIG. 1.

In this embodiment, enclosed space 502 may be held in place using flexible strap 108, placed over the head to secure the enclosed space at the oral location or ear straps, as previously described above, relative to enclosed space 102. In one embodiment, enclosed space 502 may also be used with collar 401 of FIG. 4. In this embodiment, flexible tubing 504 bridges the oral end of tube 103 to the delivery tube 105 is a manner that still allows the endotracheal tubing 103 to slide back and forth relative to enclosed space 502. In this embodiment, the enclosed space 502 is not required to be a closed enclosed space in order to practice the invention because the internal volume is not utilized as part of the delivery apparatus. In this embodiment, patient 101 does not have any part of the enclosed space inserted orally. In other embodiment, an elongated first hollow stem is used similarly to the first hollow stem 104 of FIG. 1. In this embodiment, the internal space of the enclosed space may protect the interface between the oral end of the endotracheal tube and the second stem, (not illustrated), that supports the oxygen delivery tube, 105.

In this embodiment, flex tube 504 is a flex tubing that may flex and stay open while the endotracheal tubing 103 is sliding into and out of the enclosed space 502. Fitting 503 prevents endotracheal tube 103 from coming back out of enclosed space 502 through ring 501.

In a preferred embodiment, the endotracheal attachment systems 100, 400, and 500 allow sliding the endotracheal tube into and out of the enclosed structure. the securing apparatus. In other embodiment, the endotracheal tube may have also a limited movements over of the cuff. The objective of the design is to keep the cuff or cuffs as stationary as is possible during use and to avoid dragging the cuff or cuffs over the mucosa of the trachea, preventing tracheal damage and ventilator associated pneumonias.

It will be apparent with skill in the art that the endotracheal tube attachment system of the present invention may be provided using some of, a combination of, or all the elements described herein, without departing from the spirit and scope of the present invention. The arrangement of elements and functionality thereof relative to the endotracheal tube attachment system of the invention is described in different embodiments, each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. An endotracheal tube interface apparatus comprising:
   a. an endotracheal tube having a tracheal end configured to be placed through an oral or nasal orifice of a patient into the trachea and an external oral end configured to remain outside the patient;
   b. an enclosed space structure defining an internal volume and having a rearward wall;
   c. a first hollow stem disposed on the rearward wall and having an inside diameter greater than an outside diameter of the endotracheal tube, the first hollow stem opening into the internal volume;
   d. a second hollow stem disposed on a surrounding wall of the enclosed space structure, the second hollow stem opening into the internal volume and having an inside diameter at least equal to an inside diameter of the endotracheal tube;
   e. a section of flex tubing disposed within the internal volume and attached at a first end to a fitting installed on the external oral end of the endotracheal tube and attached at a second end to the second hollow stem;
   f. a connector on the second hollow stem configured to couple to an external breathing-gas delivery tube;
   g. and a securing apparatus coupled to the enclosed space structure and configured to retain the enclosed space structure at a front portion of the patient;
   h. wherein the external oral end of the endotracheal tube extends through the first hollow stem into the internal volume and is fluidly connected via the flex tubing to the second hollow stem to receive breathing gas delivered through the external breathing-gas delivery tube, and wherein the flex tubing permits movement of the external oral end within the enclosed space structure while reducing transmission of forces to the tracheal end during relative movement of the endotracheal tube and the enclosed space structure.

2. The endotracheal tube interface apparatus of claim 1, wherein the first hollow stem comprises an elongated hollow conduit having a curvature corresponding to a Magill curve and configured to be at least partially received within the patient's mouth during use to protect the endotracheal tube from occlusion or damage due to biting.

3. The endotracheal tube interface apparatus of claim 1, wherein the enclosed structure includes at least one additional opening enabling access to the internal volume for various operations like gas delivery or manipulation of parts.

4. The endotracheal tube interface apparatus of claim 1, wherein the enclosed space structure is molded with an ergonomic shape having a rearward wall that conforms generally to a patient's mouth and chin region and accommodates the size and shape of the endotracheal tube.

5. A method of intubating and ventilating a patient, comprising:
   a. inserting a tracheal end of an endotracheal tube into a trachea of the patient, the endotracheal tube having an external oral end;
   b. inserting the external oral end through a first hollow stem of an enclosed space structure into an internal volume of the enclosed space structure;
   c. attaching, within the internal volume, a flexible tubing between a fitting on the external oral end of the endotracheal tube and a second hollow stem of the enclosed space structure;
   d. inflating a cuff of the endotracheal tube;
   e. securing the enclosed space structure to the patient using a securing apparatus;
   f. connecting a breathing-gas delivery tube to a connector of the second hollow stem to establish a continuous fluid path to the trachea;
   g. and delivering breathing gas through the breathing-gas delivery tube, through the second hollow stem and the flexible tubing, and into the endotracheal tube to ventilate the patient.

* * * * *